United States Patent
Djemai et al.

(10) Patent No.: US 12,310,815 B2
(45) Date of Patent: May 27, 2025

(54) DENTAL IMPLANT AND SELF-LOCKING FASTENING ELEMENT WITH HETEROGENEOUSPOROUS STRUCTURES, AND METHOD FOR ITS PRODUCTION

(71) Applicants: Abdelmadjid Djemai, Deuil la Barre (FR); Jean-Jacques Fouchet, Lombreuil (FR)

(72) Inventors: Abdelmadjid Djemai, Deuil la Barre (FR); Jean-Jacques Fouchet, Lombreuil (FR)

( * ) Notice: Subject to any disclaimer, the term of this patent is extended or adjusted under 35 U.S.C. 154(b) by 0 days.

(21) Appl. No.: 16/327,837

(22) PCT Filed: Nov. 30, 2016

(86) PCT No.: PCT/FR2016/053154
§ 371 (c)(1),
(2) Date: Feb. 24, 2019

(87) PCT Pub. No.: WO2018/100250
PCT Pub. Date: Jun. 7, 2018

(65) Prior Publication Data
US 2019/0290402 A1   Sep. 26, 2019

(51) Int. Cl.
*A61C 8/00* (2006.01)
*A61K 6/818* (2020.01)
*A61K 6/822* (2020.01)
*A61K 6/84* (2020.01)

(52) U.S. Cl.
CPC .......... *A61C 8/0033* (2013.01); *A61C 8/0012* (2013.01); *A61C 8/0022* (2013.01); *A61C 8/0074* (2013.01); *A61C 8/0089* (2013.01); *A61K 6/818* (2020.01); *A61K 6/822* (2020.01); *A61K 6/84* (2020.01); *A61C 2008/0046* (2013.01)

(58) Field of Classification Search
CPC ... A61C 8/0033; A61C 8/0012; A61C 8/0022; A61C 8/0074; A61C 8/0089; A61K 6/822; A61K 6/84; A61K 6/818
See application file for complete search history.

(56) References Cited

U.S. PATENT DOCUMENTS

| | | | | |
|---|---|---|---|---|
| 3,082,525 A * | 3/1963 | Christensen | ........... | A61C 8/005 433/174 |
| 3,435,526 A * | 4/1969 | Brancato | ............... | A61C 8/0048 433/174 |
| 3,497,953 A * | 3/1970 | Bernard | ............... | A61C 8/0075 433/173 |
| 4,011,602 A * | 3/1977 | Rybicki | ................ | A61F 2/3662 623/23.76 |
| 4,259,072 A * | 3/1981 | Hirabayashi | ......... | A61C 8/0012 433/173 |
| 4,842,518 A * | 6/1989 | Linkow | ................ | A61C 8/0018 433/174 |

(Continued)

*Primary Examiner* — Nicholas D Lucchesi
(74) *Attorney, Agent, or Firm* — Luis Figarella

(57) ABSTRACT

A dental implant assembly comprising an elongated inner body substantially resembling a tooth root (1-1) and an outer member for securing to a bone of a patient (1-2) having a heterogeneous porous structure adapted to provide bone growth, the inner body and the outer fixation member being formed in one piece, the fastening element being movable between a stored passive position and an extended active position (1-2).

4 Claims, 3 Drawing Sheets

(56) References Cited

U.S. PATENT DOCUMENTS

Figure 1:
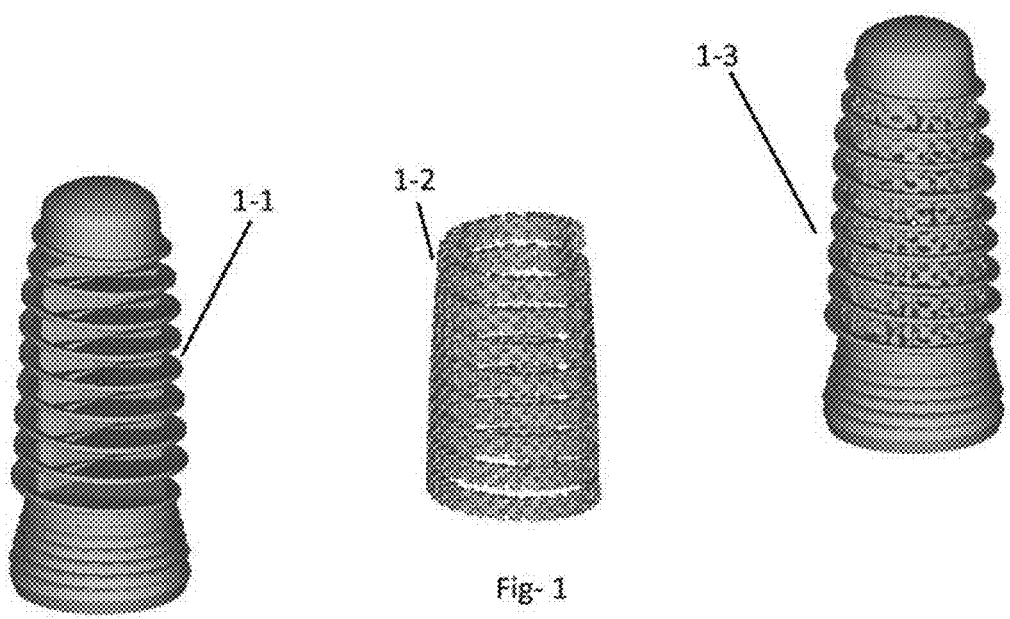

| Patent No. | | Date | Inventor | Classification |
|---|---|---|---|---|
| 5,004,421 A | * | 4/1991 | Lazarof | A61C 8/0033 433/173 |
| 5,181,850 A | * | 1/1993 | Neumeyer | A61C 8/0012 433/205 |
| 5,344,457 A | * | 9/1994 | Pilliar | A61C 8/0012 433/174 |
| 5,931,674 A | * | 8/1999 | Hanosh | A61C 8/0033 433/173 |
| 6,213,775 B1 | * | 4/2001 | Reipur | A61C 8/0033 433/173 |
| 7,281,926 B2 | * | 10/2007 | Yakir | A61C 8/001 433/173 |
| 8,231,387 B2 | * | 7/2012 | Salvi | A61C 8/0016 433/174 |
| 8,851,891 B2 | * | 10/2014 | Lomicka | A61C 8/0037 433/173 |
| 9,095,396 B2 | * | 8/2015 | Collins | A61C 8/0022 |
| 9,113,978 B2 | * | 8/2015 | Grabosch | A61C 8/005 |
| 9,744,007 B2 | * | 8/2017 | Lomicka | A61C 8/0037 |
| 9,968,423 B2 | * | 5/2018 | Lijima | A61C 8/0028 |
| 10,588,719 B2 | * | 3/2020 | Ishiwata | A61C 13/225 |
| 10,588,750 B2 | * | 3/2020 | Souza | A61F 2/28 |
| 2001/0012606 A1 | * | 8/2001 | Unger | A61C 8/0048 433/173 |
| 2003/0124486 A1 | * | 7/2003 | McDevitt | A61C 8/0033 433/167 |
| 2003/0194680 A1 | * | 10/2003 | Ristola | A61C 8/005 433/173 |
| 2008/0241793 A1 | * | 10/2008 | Collins | A61C 8/0012 433/174 |
| 2011/0111368 A1 | * | 5/2011 | Arnold | A61C 8/0033 433/174 |
| 2011/0282396 A1 | * | 11/2011 | Shimko | A61C 8/0074 606/303 |
| 2014/0222011 A1 | * | 8/2014 | Keller | F16B 21/082 606/104 |
| 2015/0125818 A1 | * | 5/2015 | Binderman | A61C 8/0078 433/173 |
| 2016/0113739 A1 | * | 4/2016 | Honig | A61C 8/0001 433/173 |
| 2017/0172709 A1 | * | 6/2017 | Iijima | A61C 8/005 |

* cited by examiner

Bones

DENTAL IMPLANT AND SELF-LOCKING FASTENING ELEMENT WITH HETEROGENEOUSPOROUS STRUCTURES, AND METHOD FOR ITS PRODUCTION

TECHNICAL AREA

A dental implant assembly includes an elongated inner body substantially resembling a root of the tooth, and a bone fixation member of a patient including a heterogeneous porous structure for bone growth.

The implant is the generally metallic infrastructure intended to support a dental prosthesis. It makes it possible to replace the natural pillars that are the teeth, by mechanical pillars, placed either in the mandibular bone, or in the maxillary bone.

The most important thing in placing a dental implant is getting an immediate block in the bone. Even a low mobility of the implant in the bone eventually leads to rejection, a small disparity between the implant and the bone can lead to bone resorption.

STATE OF THE ART AND ITS DISADVANTAGES

Current dental implant manufacturing techniques are traditional machining techniques, usually a threaded rod. The implant thus produced has a smooth and shiny surface. Once the implant is introduced into the bone, a threaded ring or screw is placed on the outer part which is generally a threaded rod. On said threaded ring or screw, is fixed by cement the dental prosthesis.

The main causes of rejection of dental implants are implant mobility (even low) and bone resorption due in general to the surface condition of the implant.
The state of the art can be defined by two categories of patents:

1) patents of implants made by machining, let us quote the patent of Jean-Marc JUILLET deposited on Jun. 12, 1972 under No. 72 21113 and published on Jan. 2, 1974 under No. 2.188.445, 2) other patents dealing with surface treatments for osteo integration, we quote the Zimmer Dental patent "Dental implant with improved osseointegration features" filed on 30 Aug. 2006 under the U.S. Pat. No. 807,512 B2.

The patent of Conformis Inc. "Devices and methods for additive manufacturing of implants components" filed Apr. 13, 2013 under the number WO 2013155500 A1

Eric's patent "Laser produced porous surfaces" filed Dec. 6, 2005 under the number US20070142914.

The patent of Howmedica Osteonics Corp. "Laser produced implants" filed Dec. 29, 2006 under the number US20080004709

All these patents describe means and methods of surface treatment or endospore deposition technique of Tantalum by the method of chemical deposition in vapor form, the porosity obtained in average of 35% and the partial inter-connectivity.

3) implant patents made by additive manufacturing (3D printing), we will quote the patent of the University of Liverpool filed on Jun. 9, 2010 under the number WO2010146383A1.

This patent discloses a dental implant made by additive manufacturing, where a method of manufacturing by selective laser melting is explained at length, but it provides no solution to the problems of locking the implant to the mouthing and thus provides no solution to avoid rejection of the implant.

Among the numerous publications dealing with the subject of the additive manufacturing of dental implants, the following are in agreement on the undeniable advantages of performing dental implants by additive manufacturing in compatible organic materials of the Ti6Al4V type in different grades:

"Direct Metal Laser Sintering Titanium Dental Implants: A Review of the Current Literature" published 1 Dec. 2014 in International Journal of Biomaterials.

"Histomorphometric Evaluation of Direct Laser Metal Forming (DLMF) Implant Surface in the Type IV Bone: A Controlled Study in Human Jaw" Published Jul. 25, 2013 in the journal POSEIDON Journal "Manufacturing of Bioactive Porous Ti Metal with Structure Similar to human Cancellous Bone by Selective Laser Melting "Published Dec. 2, 2010 in the journal BDA Bioceramics Development and Applications.

Additive manufacturing and for some additive technologies specifically (SLM, EBM, SLA) presents several possibilities for controlling geometry, porosity, inter connectivity and 3D architecture through changes in the manufacturing parameters. Main parameters for selective laser melting technology:
- the power of lasers
- the scan speed
- the diameter of the spot
- the laser route strategy
- the overlap between two melting points
- the thickness of the layers of the powder The Selective Laser Melting (SLM) selective metal powder laser melting process, the SLM name will be maintained throughout the patent text.

SLM is a process used to manufacture complex three-dimensional components from metal powders, ceramic or polymer powders. The technology is mature and already used in the aerospace and medical industry to manufacture complex components with high densities and homogeneity. We cite one of the first patents of the Fraunhofer Institute in Germany, filed Oct. 27, 1997 under the number WO1998024574A1, which describes the SLM process in a more precise way.

SUMMARY OF THE INVENTION

The invention overcomes the problems of the prior art by providing a dental implant with precise dimensions, provided with a bone fixation and growth element and a device for locking it when it is put in place.

To this end, the invention relates to a dental implant assembly comprising an elongated inner body substantially resembling a tooth root and an external member for securing a bone of a user having a heterogeneous porous structure capable of ensuring the bone growth, the inner body and the outer fixation member being formed in one piece, the fastening element being movable between a stored passive position and an extended active position.

The one-piece constitution of this assembly is furthermore obtained by means of an additive method for manufacturing the melting of powder layers, in particular the SLM process mentioned above.

The assembly according to the invention may furthermore have one and/or the other of the following characteristics:

the internal body of the implant comprises an external thread having a thread height H, the fastening element is interposed between the turns of the thread and being deployed between the stored passive position and the active position deployed by an equal distance or greater than the thread height.

The fastening element has a coefficient of thermal expansion greater than that of the body of the implant allowing it a lateral deployment greater by 15 to 40% with respect to that of the internal body at body temperature The material constituting the fixation element has a coefficient of thermal expansion greater than that of the body of the implant allowing it a lateral deployment superior from 1 to 20% at body temperature the assembly according to the invention comprises a removable device for separating the fastening element which is inserted inside the internal body and which controls the displacement of the fastening element from the passive position stowed to the position active deployed the removable spacer device is a screw for placing the implant the fastening element is connected to the inner body by a breakable connection the fastening element and the internal body have no connection the fixing element and/or the internal body consist of a composite material formed by a melting of a mixture of microparticles of a first material with a given melting point, and nanoparticles of a second material with higher melting temperature, defining an array of dendritic zones of the first material at the micron scale interspersed with nanometric filamentous zones of the second material.

the first material is a metal the second material is a ceramic the first material comprises or is titanium the second material comprises or is a zirconia the second material comprises or is an yttria zirconia The inner body has a hollow frustoconical shape defining a wall thickness, provided with an external thread, and comprises two opposite grooves made in its wall thickness and in a helical profile, the fastener element having the shape of a thick ribbon twisted according to the helical profile of the two grooves and a complementary shape to these the fixing element comprises a central longitudinal recess for passing a spacer device.

The invention also relates to the method of manufacturing an assembly as described above, by stacking layers of metal powders and/or non-metallic, selectively fused by concentration of a power source.

According to the invention, this method comprises a step of preparing the mobility of the fastening element relative to the inner body.

The method according to the invention may furthermore exhibit one or both of the following aspects:

the step of preparing the mobility of the fixing element comprises a step of forming a bridge of breakable material between a constituent part of the assembly forming the inner body and a constituent part of the assembly forming the fixing element the step of preparing the mobility of the fixing element comprises a step of constituting the part of the assembly forming the fastening element with a material having a coefficient of thermal expansion greater than that of the body of the implant allowing lateral deployment superior from 1 to 20% with respect to that of the internal body at body temperature the step of preparing the mobility of the fixing element comprises a step of forming the part of the assembly forming the inner body and the part of the assembly forming the fastening element without a material bridge between they, the part of the assembly forming the fixing element being manufactured with an internal recess allowing it to be deployable radially under the effect of a thermal expansion and/or a tool, regardless of the part of the together forming the inner body.

DETAILED DESCRIPTION OF THE FIGURES

Figure 2:
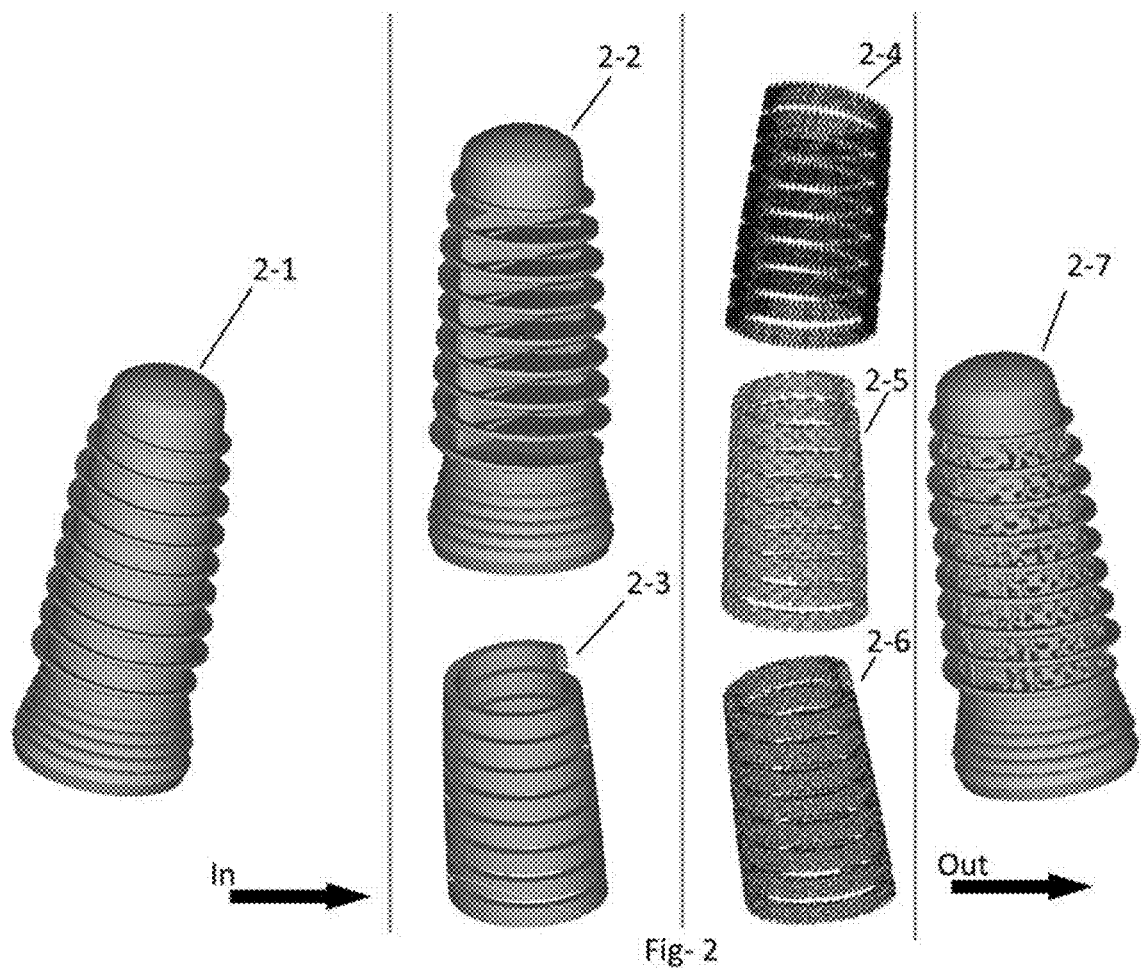

The invention will now be described in more detail with the aid of the drawings which illustrate preferred embodiments of an assembly according to the invention. On these drawings:

The FIG. 1 shows the dental implant and the fixing element according to a first exemplary embodiment The FIG. 2 Illustrates the different steps of the digital flow of the embodiment of the dental implant and fastener assembly according to FIG. 1

Figure 3:
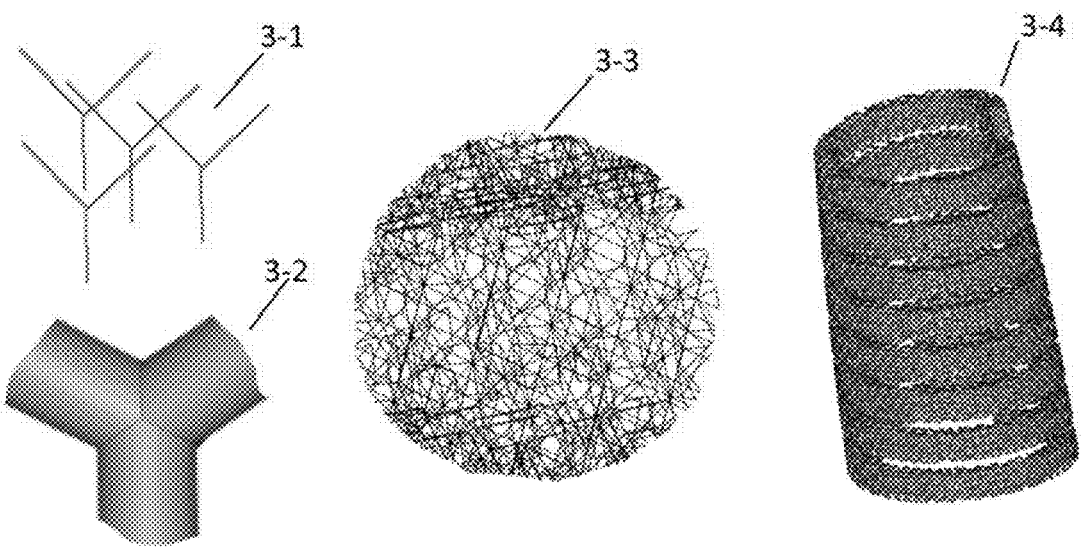

The FIG. 3 illustrates a first embodiment of the unit cell and its implementation in the fixing element of FIG. 1

Figure 4:
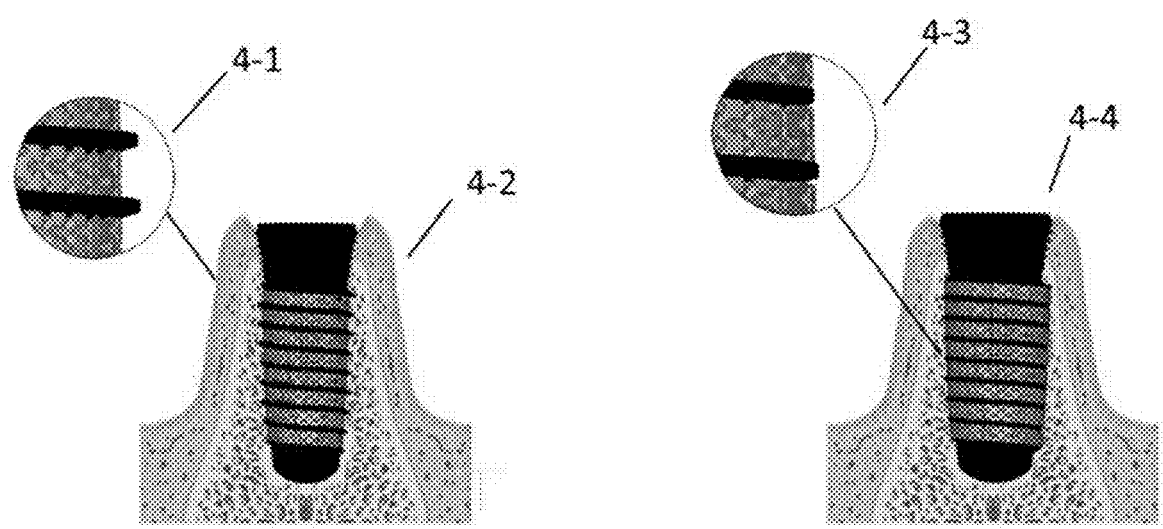

The FIG. 4 Illustrates the placement of the dental implant and fixation element (left) and its self-locking on the implant wall (on the right).

Figure 5:
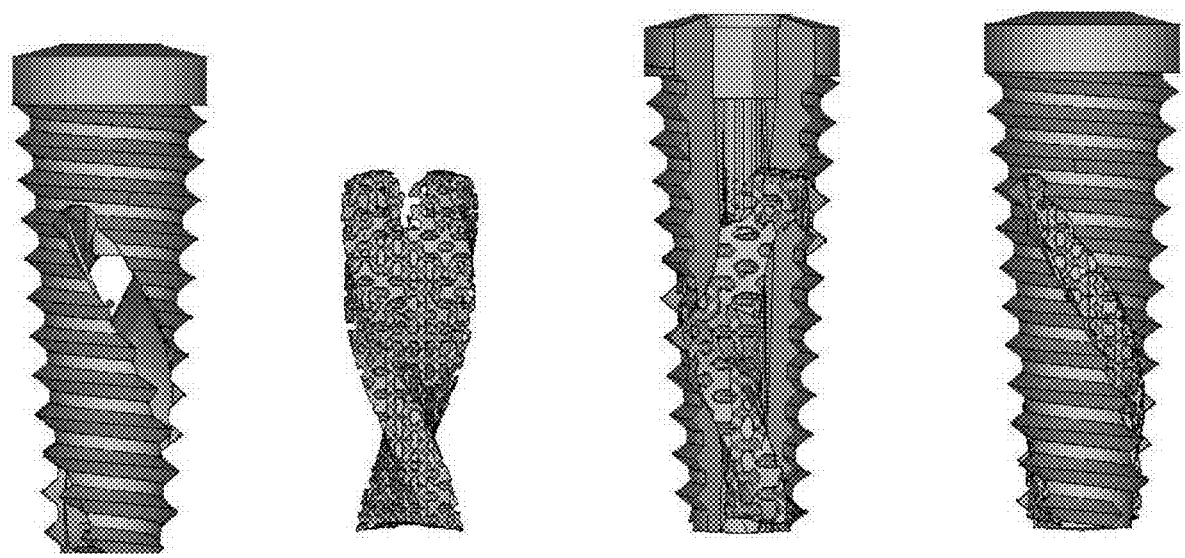
Figure 6:
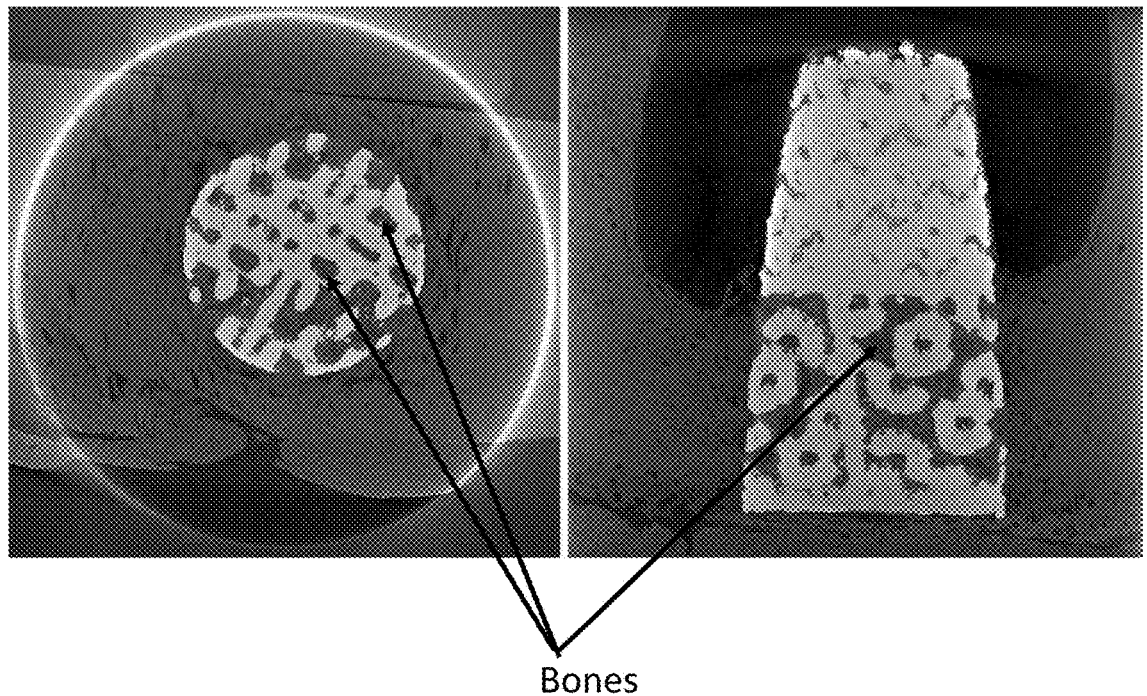

FIG. 5 illustrates a second embodiment of the dental implant assembly and fixing element according to the invention FIG. 6 represents a cross-sectional and longitudinal view of an MRI performed on a user wearing the implant of FIG. 5 after 8 weeks of bone growth (transverse section and longitudinal section, the bone being represented in dark and implant in clear)

The present invention describes a system and its method by additive manufacturing of dental implants with heterogeneous and self-locking porous structures which advantageously provides a double answer to the problems inherent in dental implantology, namely osseointegration and mobility of the implant. during his pose. For this, the present invention provides a self-locking dental implant with heterogeneous porous structures.

The dental implant described in the present invention is composed of a central body which represents the root rooted in the jawbone, the head of the implant can be rounded, flat, hollow, or any particular shape to receive the prosthetic pillar. In another embodiment, the implant may be integral with the implant abutment. The one-piece realization of the implant and the prosthetic abutment will be done by additive manufacturing, particular angles of curvature between the implant and the abutment are calculated following a digital processing of three-dimensional images of the morphology of the jaw.

It is self-locking in the bone in which it is implanted thanks to the porous bone fixation element, which is made movable between a passive row position allowing insertion of the implant into a perforation made in the bone, and a position deployed active where this porous element fills the cavities existing between the internal body of the implant and the bone and will be colonized by this bone during bone growth.

This mobility of the fastener may be caused by thermal expansion, and/or by a tool as will be explained in more detail in the following.

Porous Fastening Element

The fastener may be in the form of a heterogeneously porous helical-shaped coating for certain threaded implants, but this coating may be of different shapes and geometries that encase part or all of the implant. dental implant being preferably disposed in the portion of the dental implant in contact with the bone.

Said structure has a porosity of between 30% and 80%, a pore size of between 100 μm and 500 μm and a pore distribution of between 500 μm and 700 μm with total interconnectivity. In a preferred embodiment the porosity between 60% and 70%, the pore size between 200 microns and 300 microns with a distribution of porosity between 100 microns and 600 microns and a total inter connectivity. Its parameters are thus close to the characteristics of the human bone in the maxillary and the mandible.

Internal Body of the Implant

The body of the dental implant and its fixing element are made by stacking layers of metallic or nonmetallic powder, selectively fused together. In the case of titanium/aluminum/vanadium metal powder, the thickness of the layers is generally 30 μm. One of the additive manufacturing techniques selected for our example is SLM technology, this embodiment is not limiting, other deposition technologies can be deployed.

Achievement by Addition

A digital file of the dental implant is produced by a three-dimensional design software either according to standard models and standards or according to a particular embodiment: in this case, the shape of the dental implant, namely its height, its low section, its high section are determined more precisely.

In another embodiment, the dental implant may have the exact shape of the tooth, this mode is preferred in the case of replacement of a tooth just after extraction. A "customized" implant is thus produced according to the morphology and the mechanical properties of the tooth of the patient to be replaced and/or of the bone in which the implant will be integrated.

In this file, the fixing element is predefined with a particular thickness of between 1 and 2 mm, in a preferred embodiment the thickness is between 0.8 mm and 1.5 mm.

Several forms of porosity can be selected with the possibility of defining pore distribution zones of different sizes.

Ideally, the porous structure forming the fixing element has a porosity of between 30% and 80%, a pore size of between 100 μm and 500 μm and a pore distribution of between 500 and 700 μm with total interconnectivity.

In a preferred embodiment the porous structure has a porosity between 60% and 70%, the pore size between 200 microns and 300 microns with a distribution of porosity between 100 and 600 microns and a total inter connectivity.

The basic cell or unit cell constituting the porous structure made by stacking layers, is of geometric shape in three dimensions (x, y, z), the unit cell is formed by at least three edges with an angle opening d at least 10°, such as a trihedron, and the unit cell may be of regular or irregular shape in the form of a pyramid, tetrahedron, cubic, octahedron, icosahedron, dodecahedron and without shape limitation. In a preferred embodiment, the unit cell will be of reinforced dodecahedron form.

In another embodiment, the unit cell is formed of 12 edges with edge opening angles of 30° to the vertical axis or construction axis. The edges can be regular or irregular depending on the density of the mesh and the desired porosity.

The material used for the production of such an implant is a biocompatible material of pure metal or metal alloys of the cobalt, tantalum, niobium chromium type, metal-ceramic or organo-metal or organo-ceramic compounds or a metal organo-ceramic combination.

For the realization of the internal body, two alloys of materials have been preferentially used:
a titanium alloy aluminum vanadium Ti6Al4V grade 23, with an oxygen content<0.2%,
A combination of a titanium alloy advantageously mixed with a zirconia-based material.

For the realization of the fixing element, three alloys were used:
A titanium alloy aluminum vanadium Ti6Al4V grade 23, with an oxygen content<0.2%,
A combination of a titanium alloy advantageously mixed with a zirconia-based material
A combination of a titanium alloy advantageously mixed with a nickel-based alloy And in a preferred embodiment, the inner body and/or the porous fastener consist of a biocompatible material containing a zirconia-titanium composite/binary material with zirconia powder concentrations of between 5% and 25%, which is obtained during the shaping of this internal body and/or fastening element by additive manufacturing by selective melting of layers of powders, powders advantageously consisting of a mixture of nanometric particles of zirconia (or any other ceramics) and particles micrometric titanium (or any other metal).

Once the shapes of the inner body and of the fixing element have been determined, the porosity of the selected fastening element, the unit cell defining this porosity, also chosen, the constituent materials of these chosen, and the mobility means of the determined fastening element, the embodiment by additive manufacturing, and in a preferential mode by the SLM technology can be launched.

The dental implants system with heterogeneous porous structures is made by selective fusion of biocompatible metal powder with a particular embodiment of the implant surface.

The autoblocking system of the implant can be achieved by a mechanical means external to the implant or internal and then performed simultaneously with the implant and which pushes the helical portion to the bone seat of the implant.

The fixing element which advantageously has a helical profile in order to be distributed over the whole of the external surface of the implant, and which is made movable between the inactive, stored and deployed active positions, can be integral (a). or not integral (b) of the central nucleus or internal body of the dental implant:

(a) Solidary: the helicoidal part is held by at least four integral fixation points of the central pillar or inner body, at the laying of the dental implant, a suitable tool comes to chase the fixing points in order to release the helicoidal part which just stick to the walls of the dug out of the implant. In this case, it may be provided that the porous fastening element is made in a pre-stressed form and fixed in its pre-stressed form to the inner body by the attachment points, so that when the fixation, it can be released and expand naturally with respect to the internal body to adopt its active position deployed (b) Not secured: the assembly of the helical portion on the central pillar is for example by lateral compression by a suitable tool and the installation of the dental implant, the assembly is released.

Other means of blocking the fastening element in the hollow formed in the bone, can be envisaged, for example, the thermal fixation by thermal expansion of the fastening element when inserted into the bone. of the patient and subjected to his body temperature (it is then expected a thermal expansion of the fastener greater than that of the internal body of the implant, at least 20% for example) or chemical fixation in reaction to an additive or in contact with the implant medium. For example, the fastener may be a moisture-responsive polymer that will swell when exposed to the moisture of the patient's body once inserted into the bone.

Another mode of blocking can be envisaged, with a stoichiometric mixture of nickel/titanium forming Nitinol, a shape memory alloy which has a coefficient of thermal expansion and elasticity higher than titanium. In this case, the porous fixing element may consist of Nitinol and the internal titanium body.

First Illustrated Embodiment

The dental implant described in the present invention is composed of a central body which represents the core of the implant (1-1), the head of the central body may be rounded, flat, hollow, or any particular shape to receive a implantary abutment, in another mode the implant core may be integral with the implant abutment and made in one piece in additive manufacturing with particular angles of curvature according to the morphology.

A coating with heterogeneous porous structures (1-2) of helical shape for some implants but this coating can be of different shapes and geometries that come in dressing of part or all of the dental implant.

In the example of FIG. 1, the inner body 1-1 has a frustoconical shape consisting of a flared base, a rounded head and an intermediate portion formed by a vertical plate whose side edges are crossed by a flat strip arranged in a spiral shape, as best seen in FIG. 2 under the reference 2-2. The porous fastening element here consists of a spiral-shaped strip, complementary to the turn formed by that of the inner body and interposed between the outer edges of two consecutive turns. This FIG. 1 shows an exploded view of the implant according to the invention knowing that it is preferably obtained in one piece with its inner body and its porous fastening element nested one inside the other.

FIG. 2 represents the preliminary steps to the actual realization, steps of definition of basic shapes from which to realize the object. Thus, it is defined numerically the external envelope of the implant to be made without worrying about the internal structure of the body as described above, nor the pores of the fixing element.

The particular structure of the inner body (2-2) and that of the fastening element are then defined, again without the pores (2-3).

Different porosities are then defined for the fastener (2-4, 2-5, 2-6).

And after having chosen the porosity adapted to the particular case (as a function of the mechanical properties envisaged with such a structure and such porosity), a file is defined which joins the particular internal body with its complete structure, and the fixing element with porosity. desired (2-7).

The implant is then made by additive manufacturing according to the SLM technology already described, the implant (2-1) is made by a three-dimensional design software according to the morphology of the patient, the height and the section of the implant are thus defined.

In this example, the fixing element is made movable between the position shown in FIG. 4 on the left: passive position row, and the active position deployed (FIG. 4 right) in that it is independent (unbound) to internal body, and consisting of a material having a coefficient of thermal expansion greater than 15 to 40%, preferably 15 to 25% of that of the material constituting the inner body, at body temperature (of the order of 37° C.). One could also provide a fastening element made integral with the inner body by securing points breakable from a threshold, crossed threshold when the fastener expands thermally exposed to the body temperature of the user. We will then choose the material according to this threshold.

In this case, the fastening element expands so that its outer wall flushes the ridges of the flat spiral band of the body and thus comes into contact with no gap in the bone cavity.

It can be provided that the fastening element is connected to the body by a bridge of breakable material (for example of smaller thickness) or a chemical bridge.

Or that the fastening element can be spaced radially relative to the inner body that contains it.

This is the embodiment shown in FIG. 5.

The porous part (2-3) is predefined with a particular thickness of between 1 and 2 mm from the central body of the implant (2-2).

Several porosity shapes can be selected (2-4; 2-5; 2-6) with the possibility of setting the pore distribution zones of different sizes.

The basic cell or unit cell (3) is of geometric shape in three dimensions (x, y, z), the unit cell is formed by at least three edges (3-1), with a rounded-shaped cladding (3-). 2), this form is not limiting, with an angle opening of at least 10°, and the unit cell may be of regular or irregular shape in the form of a pyramid, tetrahedron, cubic, octahedron, icosahedron, dodecahedron and without limitation of form.

The distribution of unit cells (3-3) can be regular or irregular, with opening angles of at least 10°. After dressing the unit cells (3-4) the porous part is formed.

An implant diameter drill tapped the bone, because of the low density and natural porosity of the maxillary and mandibular bone, the threading is approximate. At the mouth of the dental implant (4-2), small cavities appear between the body of the implant and the bone see detail (4-1). Upon release of the fastener (4-4) all small cavities are filled, see detail (4-3).

The numerical execution flow of tasks is summarized in FIG. 2:

Step 1: The digital file of the dental implant is made by a three-dimensional design software (2-1), the shape can be standardized according to a pre-defined or customizable model.

Step 2: delimiting the part of the fixation element (2-3) and the solid part representing the body of the implant (2-2), Step 3: Generate a type of unit cells or a combination of said base cells (2-4; 2-5; 2-6). Which cells are characterized by the geometry thus produced has the advantage of controlling the porosity and its density.

Step 4: Realization of the central implant assembly+fixing element (2-7) having a porous surface advantageously heterogeneous.

Second Embodiment

In this example, the inner body (5-1) has a hollow frustoconical shape defining a wall thickness, provided with an external thread 5-2, and comprises two opposite grooves 5-3 made in its wall thickness and following a helicoidal profile, the fastening element 5-4 having the shape of a thick ribbon twisted according to the helical profile of the two grooves and a shape complementary to those ci.

The fastening element 3-4 comprises an upper and central longitudinal recess 5-5 for the passage of a spacer, such as the screw for placing the implant.

The first two views of this FIG. 5 separately represent the inner body 5-1 and the fastening element 5-4 for a better understanding of their structure, but the one-piece form is the one shown in tearing view and in normal view on the third and fourth view.

It can be seen in FIG. 6, which shows a cross-sectional and longitudinal view of an MRI performed on a user wearing an implant according to the invention after 8 weeks of bone growth, that the bone has penetrated deeply into the heart of the bone. implant, and that the bone portion having penetrated the implant is of equivalent quality to that of the cortical bone surrounding the implant and therefore of good quality.

Example of the implant parameters of the Dental Implant and Fixation Device Set on an SLM 125 HL machine from the manufacturer SLM SOLUTIONS GMBH

| Parameter type Dental implant Fixing element | Parameter type Dental implant Fixing element | Parameter type Dental implant Fixing element |
|---|---|---|
| Powder type Titanium (Ti6Al4V) Titanium (Ti6Al4V) | Powder type Titanium (Ti6Al4V) Titanium (Ti6Al4V) | Powder type Titanium (Ti6Al4V) Titanium (Ti6A14V) |
| Laser power in full area (w) 400, 300 | Laser power in full area (w) 400 300 | Laser power in full area (w) 400 300 |
| Laser low power (w) 200 100 | Laser low power (w) 200 100 | Laser low power (w) 200 100 |
| Laser power in porous zone (w) 100 | Laser power in porous zone (w) 100 | Laser power in porous zone (w) 100 |
| Exposure (ms) 350 380 | Exposure (ms) 350 380 | Exposure (ms) 350 380 |
| Exposure limit (ms) 300 350 | Exposure limit (ms) 300 350 | Exposure limit (ms) 300 350 |
| Hatching distance (μm) 25 10 | Hatching distance (μm) 25 10 | Hatching distance (μm) 25 10 |
| Powder type Titanium/zirconia Titanium/nickel | Powder type Titanium/zirconia Titanium/nickel | Powder type Titanium/zirconia Titanium/nickel |
| Laser power in full area (w) 400 200 | Laser power in full area (w) 400 200 | Laser power in full area (w) 400 200 |
| Low power of the laser (w) 200 80 | Low power of the laser (w) 200 80 | Low power of the laser (w) 200 80 |
| Laser power in porous zone (w) 80 | Laser power in porous zone (w) 80 | Laser power in porous zone (w) 80 |
| Exposure (ms) 350 380 | Exposure (ms) 350 380 | Exposure (ms) 350 380 |
| Exposure limit (ms) 300 350 | Exposure limit (ms) 300 350 | Exposure limit (ms) 300 350 |
| Hatching distance (μm) 25 10 | Hatching distance (μm) 25 10 | Hatching distance (μm) 25 10 |
| Powder type Titanium/zirconia Titanium/zirconia | Powder type Titanium/zirconia Titanium/zirconia | Powder type Titanium/zirconia Titanium/zirconia |
| Laser power in full area (w) 400 400 | Laser power in full area (w) 400 400 | Laser power in full area (w) 400 400 |
| Low power of the laser (w) 200 125 | Low power of the laser (w) 200 125 | Low power of the laser (w) 200 125 |
| Laser power in porous zone (w) 125 | Laser power in porous zone (w) 125 | Laser power in porous zone (w) 125 |
| Exposure (ms) 380 400 | Exposure (ms) 380 400 | Exposure (ms) 380 400 |
| Exposure limit (ms) 280 320 | Exposure limit (ms) 280 320 | Exposure limit (ms) 280 320 |
| Hatching distance (μm) 30 25 | Hatching distance (μm) 30 25 | Hatching distance (μm) 30 25 |

Preferably, it is recalled that:

the assembly according to the invention is produced by stacking layers of metallic or non-metallic powders, fused selectively by concentration of a source of energy.

the assembly according to the invention is characterized in that said fixing element comprises a heterogeneous structure having a porosity of between 60% and 80%.

the assembly according to the invention is characterized in that said fixing element is formed by a multiple of a unit cell, said unitary cell is formed by at least three edges and opening angles of at least 10°.

the assembly according to the invention is characterized in that said dental implant has either a cylindric-conical geometry or the morphological shape of the tooth.

the preferred material according to the invention is derived from the fusion of a homogeneous and stable mixture of microscopic titanium or Ti6Al4V powders and nanoscopic yttria zirconia powders in which:

the content of titanium or Ti6Al4V is between 60 and 95.5% with a particle size of between 5 and 10 microns the yttria zirconia content is between 13.5 and 30% with a particle size of between 30 and 70 nm and a median size of between 65 and 85 nm and a minimum size of greater than 20 nm.

The invention claimed is:

1. A dental implant assembly created through an additive manufacturing process, said assembly comprising:
   an elongated body;
   said elongated body substantially resembling a tooth root and an outer member for fixing a heterogeneous porous structure to a patient's bone structure adapted to provide bone growth;
   the outer member being comprised of heterogenous porous structure movable between a stored passive position and an extended active position; and
   wherein said body and said outer member are formed in one piece from the same material through an additive manufacturing process using only dry powder materials.

2. The dental implant assembly of claim 1 wherein:
   said body of the implant assembly comprises an external thread having a thread height H, said outer member is interposed between the turns of the thread and unfolding between the stored passive position and the extended active position by a distance equal to or greater than said thread height.

3. The dental implant assembly of claim 2 wherein:
   said outer member has a coefficient of thermal expansion greater than 15 to 40% of that of the body of said implant assembly at body temperature allowing said implant assembly a greater lateral deployment.

4. The dental implant assembly of claim 2, wherein:
   the material constituting said outer member has a coefficient of thermal expansion greater than 15 to 40% of that of the body of said implant assembly at body temperature allowing said implant assembly a greater lateral deployment.

* * * * *